United States Patent
Weiner et al.

(10) Patent No.: US 9,050,287 B2
(45) Date of Patent: Jun. 9, 2015

(54) VACCINES FOR HUMAN PAPILLOMA VIRUS AND METHODS FOR USING THE SAME

(75) Inventors: David B Weiner, Merion, PA (US); Jian Yan, Haverford, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 366 days.

(21) Appl. No.: 13/271,576

(22) Filed: Oct. 12, 2011

(65) Prior Publication Data

US 2012/0053509 A1 Mar. 1, 2012

Related U.S. Application Data

(63) Continuation-in-part of application No. 12/691,588, filed on Jan. 21, 2010, now Pat. No. 8,389,706.

(60) Provisional application No. 61/146,942, filed on Jan. 23, 2009.

(51) Int. Cl.

| C07H 21/02 | (2006.01) |
|---|---|
| C07K 14/00 | (2006.01) |
| A61K 39/295 | (2006.01) |
| A61K 39/12 | (2006.01) |
| C07K 14/005 | (2006.01) |
| A61K 39/00 | (2006.01) |

(52) U.S. Cl.
CPC ............. *A61K 39/12* (2013.01); *A61K 2039/53* (2013.01); *C07K 14/005* (2013.01); *C12N 2710/20022* (2013.01); *C12N 2710/20034* (2013.01); *C12N 2800/22* (2013.01)

(58) Field of Classification Search
CPC ............. A61K 2300/00; A61K 39/00; A61K 2039/53; C12Q 1/708
See application file for complete search history.

(56) References Cited

U.S. PATENT DOCUMENTS

| 4,510,245 A | 4/1985 | Cousens et al. |
|---|---|---|
| 4,722,848 A | 2/1988 | Paoletti et al. |
| 4,790,987 A | 12/1988 | Compans et al. |
| 4,797,368 A | 1/1989 | Carter et al. |
| 4,920,209 A | 4/1990 | Davis et al. |
| 4,945,050 A | 7/1990 | Sanford et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey, III et al. |
| 5,174,993 A | 12/1992 | Paoletti |
| 5,223,424 A | 6/1993 | Cochran et al. |
| 5,225,336 A | 7/1993 | Paoletti |
| 5,240,703 A | 8/1993 | Cochran |
| 5,242,829 A | 9/1993 | Panicali et al. |
| 5,294,441 A | 3/1994 | Curtiss, III |
| 5,294,548 A | 3/1994 | McLinden et al. |
| 5,310,668 A | 5/1994 | Ellis et al. |
| 5,387,744 A | 2/1995 | Curtiss, III et al. |
| 5,389,368 A | 2/1995 | Curtiss, III |
| 5,424,065 A | 6/1995 | Curtiss, III et al. |
| 5,451,499 A | 9/1995 | Cochran |
| 5,453,364 A | 9/1995 | Paoletti |
| 5,462,734 A | 10/1995 | Letchworth, III et al. |
| 5,470,734 A | 11/1995 | Sondermeijer et al. |
| 5,474,935 A | 12/1995 | Chatterjee et al. |
| 5,482,713 A | 1/1996 | Paoletti |
| 5,580,859 A | 12/1996 | Felgner et al. |
| 5,591,439 A | 1/1997 | Plotkin et al. |
| 5,593,972 A | 1/1997 | Weiner et al. |
| 5,643,579 A | 7/1997 | Hung et al. |
| 5,650,309 A | 7/1997 | Wong-Staal et al. |
| 5,676,594 A | 10/1997 | Joosten |
| 5,698,202 A | 12/1997 | Ertl et al. |
| 5,703,055 A | 12/1997 | Felgner et al. |
| 5,739,118 A | 4/1998 | Carrano et al. |
| 5,817,637 A | 10/1998 | Weiner et al. |
| 5,830,876 A | 11/1998 | Weiner et al. |
| 5,955,088 A | 9/1999 | Ghiasi et al. |
| 5,962,428 A | 10/1999 | Carrano et al. |
| 5,981,505 A | 11/1999 | Weiner et al. |
| 6,034,298 A | 3/2000 | Lam et al. |
| 6,042,836 A | 3/2000 | Berman et al. |
| 6,156,319 A | 12/2000 | Cohen et al. |
| 6,365,160 B1 * | 4/2002 | Webb et al. ................. 424/192.1 |
| 6,589,529 B1 | 7/2003 | Choi et al. |
| 7,245,963 B2 | 7/2007 | Draghia-Akli et al. |
| 8,221,970 B2 * | 7/2012 | Chau et al. ........................ 435/5 |
| 2005/0031638 A1 | 2/2005 | Dalemans |
| 2005/0052630 A1 | 3/2005 | Smith |
| 2010/0189730 A1 | 7/2010 | Weiner |

FOREIGN PATENT DOCUMENTS

| WO | WO9416737 | 8/1994 |
|---|---|---|
| WO | WO2007119896 | 10/2007 |

OTHER PUBLICATIONS

Yan et al. (Vaccine, Apr. 14, 2008, p. 5210-5215).*
Andre, S., et al,. "Increased immune response elicited by DNA vaccination with a synthetic gp120 sequence with optimized codon usage", J Virol, 1998, 72(2): 1497-503.
Dernl, L., et al., "Multiple effects of codon usage optimization on expression and immunogenicity of DNA candidate vaccines encoding the human immunodeficiency virus type 1 Gag protein.", J Virol, 2001, 75(22): 10991-11001.
Laddy, D.J., et al., "Immunogenicity of novel consensus-based DNA vaccines against avian influenza."Vaccine, 2007, 25(16): 2984-2989.
Frelin, L., et al., "Codon optimization and mRNA amplification effectively enhances the immunogenicity of the hepatitis C virus nonstructural 3/4A gene." Gene Ther, 2004, 11(6): 522-533.
Mahdavi, et al. "Vaccines Against Human Papillomavirus and Cervical Cancer . . . ", The Oncologist,2005, 10(7):528-538.

* cited by examiner

*Primary Examiner* — Agnieszka Boesen
(74) *Attorney, Agent, or Firm* — Riverside Law LLP

(57) ABSTRACT

Improved anti-HPV immunogens and nucleic acid molecules that encode them are disclosed. Immunogens disclosed include those having consensus HPV 6, HPV 11, HPV 33 and HPV58 E6 and E7. Pharmaceutical composition, recombinant vaccines comprising and live attenuated vaccines are disclosed as well methods of inducing an immune response in an individual against HPV are disclosed.

24 Claims, 6 Drawing Sheets

Fig. 1A
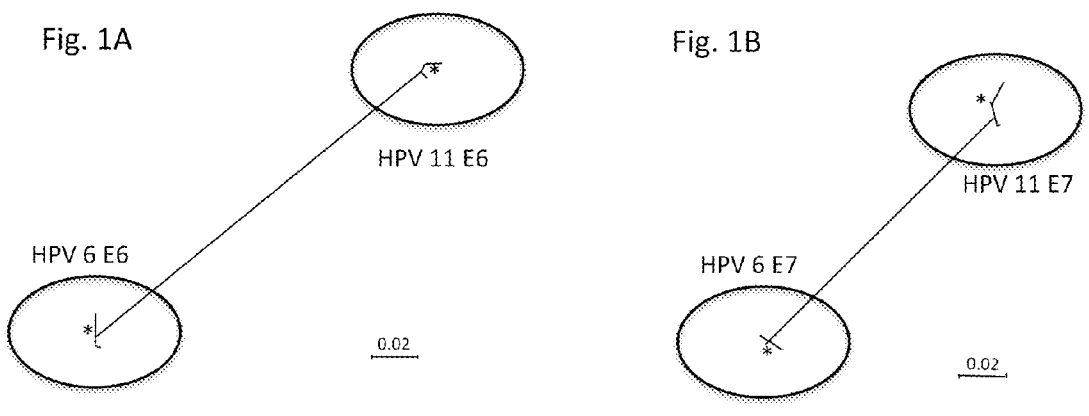
Fig. 1B
Fig. 1C
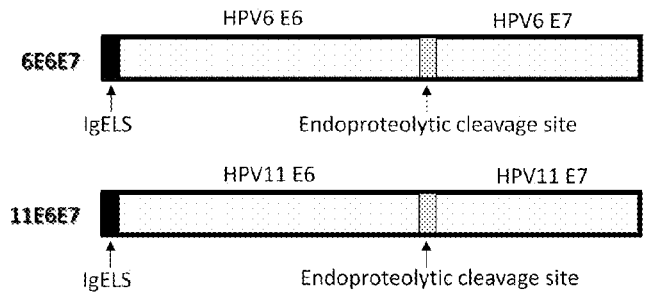

VACCINES FOR HUMAN PAPILLOMA VIRUS AND METHODS FOR USING THE SAME

This application is a Continuation-In-Part of U.S. patent application Ser. No. 12/691,588, filed Jan. 21, 2010, and claims priority to U.S. Provisional Application No. 61/146,942, filed Jan. 23, 2009, the disclosures of which are each incorporated herein by reference.

FIELD OF THE INVENTION

The present invention relates to improved human papillomavirus (HPV) vaccines, improved methods for inducing immune responses, and for prophylactically and/or therapeutically immunizing individuals against HPV.

BACKGROUND OF THE INVENTION

Papillomavirus are small DNA viruses that comprise up to seven early genes and two late genes. Generally, papilloma virus early genes are designated E1-E7, and papilloma virus late genes are designated L1 and L2. Several species of animals can be infected by members of the papillomavirus family.

Human Papillomavirus (HPV) infection is common and can be transmitted sexually. HPV have been differentiated into 56 or more types based upon DNA sequence homology. HPV types 16 and 18, which cause epithelial dysplasia and other lesions, are often associated with an increased risk of cancer, particularly in situ and invasive carcinomas of the cervix, vagina, vulva and anal canal. Nearly 88% of cervical cancers worldwide are the result of HPV subtypes 16, 18, 45, 31, 33, 52 and 58. Furthermore, various studies have revealed the presence of HPV6 and HPV11 in most incidences of recurrent respiratory papillomatosis. Though known for their association with genital warts and only found in a small percentage of cervical cancer cases, HPV6 and HPV11 have been found in 2.6-5.2% of all cases of low-grade cervical lesions. Furthermore, HPV6 and HPV11 have now been associated with approximately 20% of low-grade squamous intraepithelial lesions that are now considered precursors to cervical cancer, including grade 2 and 3 cervical intraepithelial neoplasia and mild cervical dysplasia. Increasing studies have revealed the association of the two serotypes with various forms of otolaryngologic diseases, including genital warts, recurrent respiratory papillomatosis, lung carcinoma, tonsillar carcinoma, laryngeal carcinoma, and other malignant transformations of otherwise benign neoplasms and dysplasia of the head and neck. The findings of this study shed light and future promise in the use of consensus sequence DNA vaccines against HPV6 and HPV11.

DNA vaccines have many conceptual advantages over more traditional vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platforms immunogenicity when moving to larger animals [Liu, M. A. and J. B. Ulmer, Human clinical trials of plasmid DNA vaccines. Adv Genet, 2005. 55: p. 25-40]. Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. In addition, studies have suggested that the use of consensus immunogens may be able to increase the breadth of the cellular immune response as compared to native antigens alone [Yan., J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

There remains a need for improved vaccines and methods for preventing and treating HPV infection, in particular infections leading to cervical cancer and/or carcinomas of the lung, tonsil, and larynx.

SUMMARY OF THE INVENTION

Aspects of the present invention include nucleic acid molecules comprising a nucleotide sequence encoding for an HPV antigen selected from the group consisting of: SEQ ID NO:1; SEQ ID NO:3, SEQ ID NO:5, SEQ ID NO:7; fragments thereof having 90% homology; and combinations thereof. In some aspects, the nucleic acid molecules comprise nucleic acid molecules comprising a nucleotide sequence selected from the group consisting of: nucleotide sequences that encode SEQ ID NO:2; SEQ ID NO:4, SEQ ID NO:6, or SEQ ID NO:8; nucleotide sequences that encode an amino acid fragments having at least 90% homology to SEQ ID NO:2; SEQ ID NO:4, SEQ ID NO:6, or SEQ ID NO:8; fragments of nucleotide sequences that encode SEQ ID NO:2; SEQ ID NO:4, SEQ ID NO:6, or SEQ ID NO:8; and fragments of a nucleotide sequence that encode an amino acid fragment having at least 90% homology to SEQ ID NO:2; SEQ ID NO:4, SEQ ID NO:6, or SEQ ID NO:8.

In some aspects, there are pharmaceutical compositions comprising a nucleic acid molecule described herein.

In other aspects, there are provided methods of inducing an immune response in an individual against HPV comprising administering to said individual a composition comprising a nucleic acid molecule described herein.

The present invention also includes recombinant vaccines comprising a nucleic acid molecule described herein. The recombinant vaccines include recombinant vaccinia vaccine, live attenuated vaccine, and DNA plasmids.

Some aspects of the present invention include proteins comprising an amino acid sequence selected from the group consisting of: SEQ ID NO:2; SEQ ID NO:4, SEQ ID NO:6, or SEQ ID NO:8; and fragments of sequences having at least 90% homology to SEQ ID NO:2; SEQ ID NO:4, SEQ ID NO:6, or SEQ ID NO:8.

There are also provided methods of inducing an immune response in an individual against HPV comprising administering to said individual a recombinant vaccine provided herein.

In some aspects, there are provided pharmaceutical compositions comprising nucleotide sequences encoding for an HPV antigen SEQ ID NO:1 and SEQ ID NO:3; or fragments thereof; or fragments having 90% homology thereof. There are also methods of inducing an immune response in an individual against HPV subtypes 6 or 11 comprising administering to said individual the aforementioned pharmaceutical compositions.

In some aspects, there are provided pharmaceutical compositions comprising nucleotide sequences encoding for an HPV antigen SEQ ID NO:5 and SEQ ID NO:7; or fragments thereof; fragments having 90% homology thereof. There are also methods of inducing an immune response in an individual against HPV subtypes 33 or 58 comprising administering to said individual the aforementioned pharmaceutical compositions.

BRIEF DESCRIPTION OF THE FIGURE

FIG. 1. Phylogenetic trees based on neighbor joining evaluation of E6 and E7 alignments (A and B, respectively). Asterisks indicate location of consensus sequences on each tree. Modifications conducted after generating the consensus E6/E7 fusion sequence (C).

DETAILED DESCRIPTION OF PREFERRED EMBODIMENTS

Figure 2A:
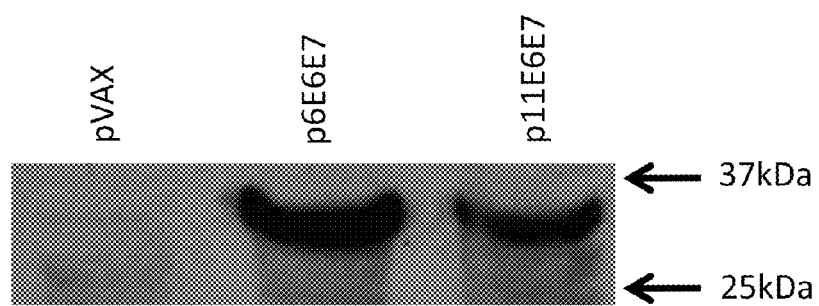
FIG. 2. In vivo expression of p6E6E7 and p11E6E7. Gene products were isolated from lysed transfected 293-T cells, run through SDS-PAGE gel, and detected using autoradiography. Both HPV 6 and HPV 11 E6/E7 proteins are approximately 32 kDa each (A). Human rhabdomyosarcoma (RD) cells were also transfected with p6E6E7 and p11E6E7 and later fixed after immunofluorescence staining FITC fluorescence confirms expression of p6E6E7 and p11E6E7(B). DAPI fluorescence confirms nuclei localization consequent of Hoescht staining.
Figure 2B:
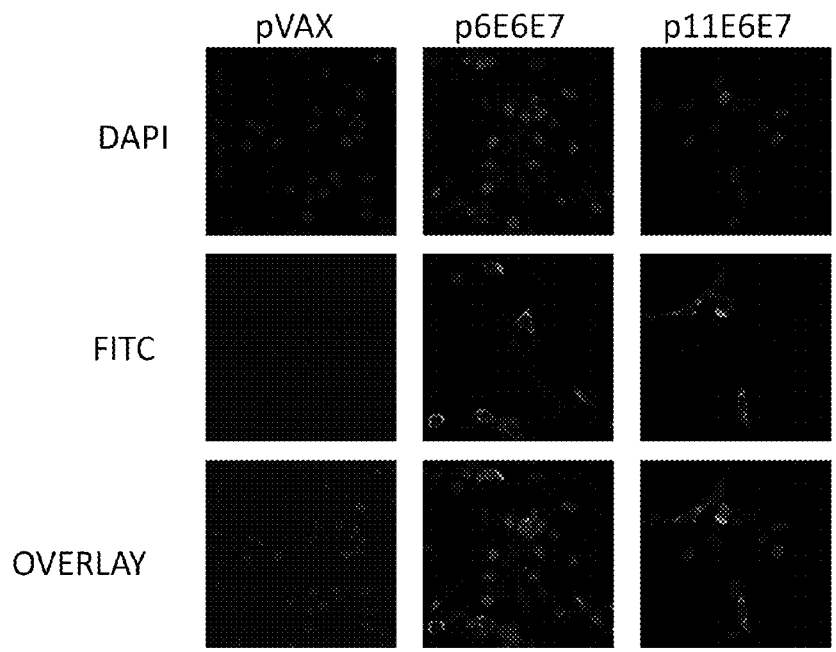

As used herein, the phrase "stringent hybridization conditions" or "stringent conditions" refers to conditions under which a nucleic acid molecule will hybridize another nucleic acid molecule, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

Sequence homology for nucleotides and amino acids may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). "Percentage of similarity" is calculated using PAUP* 4.0b10 software (D. L. Swofford, Sinauer Associates, Massachusetts). The average similarity of the consensus sequence is calculated compared to all sequences in the phylogenic tree.

Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001.

As used herein, the term "genetic construct" refers to the DNA or RNA molecules that comprise a nucleotide sequence which encodes protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a protein such that when present in the cell of the individual, the coding sequence will be expressed.

Improved vaccine are disclosed which arise from a multiphase strategy to enhance cellular immune responses induced by immunogens. Modified consensus sequences were generated. Genetic modifications including codon optimization, RNA optimization, and the addition of a high efficient immunoglobin leader sequence are also disclosed. The novel construct has been designed to elicit stronger and broader cellular immune responses than a corresponding codon optimized immunogens.

The improved HPV vaccines are based upon proteins and genetic constructs that encode proteins with epitopes that make them particularly effective as immunogens against which anti-HPV can be induced. Accordingly, vaccines may induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

According to some embodiments, a vaccine is delivered to an individual to modulate the activity of the individual's immune system and thereby enhance the immune response against HPV. When a nucleic acid molecule that encodes the protein is taken up by cells of the individual the nucleotide sequence is expressed in the cells and the protein are thereby delivered to the individual. Methods of delivering the coding sequences of the protein on nucleic acid molecule such as plasmid, as part of recombinant vaccines and as part of attenuated vaccines, as isolated proteins or proteins part of a vector are provided.

Compositions and methods are provided which prophylactically and/or therapeutically immunize an individual against HPV.

Compositions for delivering nucleic acid molecules that comprise a nucleotide sequence that encodes the immunogen are operably linked to regulatory elements. Compositions may include a plasmid that encodes the immunogen, a recombinant vaccine comprising a nucleotide sequence that encodes the immunogen, a live attenuated pathogen that encodes a protein of the invention and/or includes a protein of the invention; a killed pathogen includes a protein of the invention; or a composition such as a liposome or subunit vaccine that comprises a protein of the invention. The present invention further relates to injectable pharmaceutical compositions that comprise compositions.

SEQ ID NO:1 comprises a nucleotide sequence that encodes a consensus immunogen of HPV 6 E6 and E7 proteins. SEQ ID NO:1 includes an IgE leader sequence SEQ ID NO:9 linked to the nucleotide sequence at the 5' end of SEQ ID NO:1. SEQ ID NO:2 comprises the amino acid sequence for the consensus immunogen of HPV 6 E6 and E7 proteins. SEQ ID NO:2 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:2, or a nucleic acid molecule that encodes SEQ ID NO:2.

In some embodiments, fragments of SEQ ID NO:1 may comprise 786 or more nucleotides; in some embodiments, 830 or more nucleotides; in some embodiments 856 or more nucleotides; and in some embodiments, 865 or more nucleotides. In some embodiments, fragments of SEQ ID NO:1 such as those set forth herein may further comprise coding sequences for the IgE leader sequences. In some embodiments, fragments of SEQ ID NO:1 do not comprise coding sequences for the IgE leader sequences.

In some embodiments, fragments of SEQ ID NO:2 may comprise 252 or more amino acids; in some embodiments, 266 or more amino acids; in some embodiments, 275 or more amino acids; and in some embodiments, 278 or more amino acids.

SEQ ID NO:3 comprises a nucleotide sequence that encodes a consensus immunogen of HPV 11 E6 and E7 proteins. SEQ ID NO:3 includes an IgE leader sequence SEQ ID NO:9 linked to the nucleotide sequence at the 5' end of SEQ ID NO:3. SEQ ID NO:4 comprises the amino acid sequence for the consensus immunogen of HPV 11 E6 and E7 proteins. SEQ ID NO:4 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:4, or a nucleic acid molecule that encodes SEQ ID NO:4.

In some embodiments, fragments of SEQ ID NO:3 may comprise 786 or more nucleotides; in some embodiments, 830 or more nucleotides; in some embodiments 856 or more nucleotides; and in some embodiments, 865 or more nucleotides. In some embodiments, fragments of SEQ ID NO:3 such as those set forth herein may further comprise coding sequences for the IgE leader sequences. In some embodiments, fragments of SEQ ID NO:3 do not comprise coding sequences for the IgE leader sequences.

In some embodiments, fragments of SEQ ID NO:4 may comprise 252 or more amino acids; in some embodiments, 266 or more amino acids; in some embodiments, 275 or more amino acids; and in some embodiments, 278 or more amino acids.

SEQ ID NO:5 comprises a nucleotide sequence that encodes a consensus immunogen of HPV 33 E6 and E7 proteins. SEQ ID NO:5 includes an IgE leader sequence SEQ ID NO:9 linked to the nucleotide sequence at the 5' end of SEQ ID NO:5. SEQ ID NO:6 comprises the amino acid sequence for the consensus immunogen of HPV 33 E6 and E7 proteins. SEQ ID NO:6 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:6, or a nucleic acid molecule that encodes SEQ ID NO:6.

In some embodiments, fragments of SEQ ID NO:5 may comprise 746 or more nucleotides; in some embodiments, 787 or more nucleotides; in some embodiments 812 or more nucleotides; and in some embodiments, 820 or more nucleotides. In some embodiments, fragments of SEQ ID NO:5 such as those set forth herein may further comprise coding sequences for the IgE leader sequences. In some embodiments, fragments of SEQ ID NO:5 do not comprise coding sequences for the IgE leader sequences.

In some embodiments, fragments of SEQ ID NO:6 may comprise 235 or more amino acids; in some embodiments, 248 or more amino acids; in some embodiments, 256 or more amino acids; and in some embodiments, 259 or more amino acids.

SEQ ID NO:7 comprises a nucleotide sequence that encodes a consensus immunogen of HPV 58 E6 and E7 proteins. SEQ ID NO:7 includes an IgE leader sequence SEQ ID NO:9 linked to the nucleotide sequence at the 5' end of SEQ ID NO:7. SEQ ID NO:8 comprises the amino acid sequence for the consensus immunogen of HPV 58 E6 and E7 proteins. SEQ ID NO:8 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:8, or a nucleic acid molecule that encodes SEQ ID NO:8.

In some embodiments, fragments of SEQ ID NO:7 may comprise 752 or more nucleotides; in some embodiments, 794 or more nucleotides; in some embodiments 819 or more nucleotides; and in some embodiments, 827 or more nucleotides. In some embodiments, fragments of SEQ ID NO:7 such as those set forth herein may further comprise coding sequences for the IgE leader sequences. In some embodiments, fragments of SEQ ID NO:7 do not comprise coding sequences for the IgE leader sequences.

In some embodiments, fragments of SEQ ID NO:8 may comprise 235 or more amino acids; in some embodiments, 249 or more amino acids; in some embodiments, 257 or more amino acids; and in some embodiments, 260 or more amino acids.

According to some embodiments, methods of inducing an immune response in individuals against an immunogen comprise administering to the individual the amino acid sequence for a consensus immunogen selected from the group consisting of HPV 6 E6 and E7, HPV 11 E6 and E7, HPV 33 E6 and E7, HPV 58 E6 and E7, functional fragments thereof, and expressible coding sequences thereof. Some embodiments comprise an isolated nucleic acid molecule that encodes the amino acid sequence for a consensus immunogen selected from the group consisting of HPV 6 E6 and E7, HPV 11 E6 and E7, HPV 33 E6 and E7, HPV 58 E6 and E7, and fragments thereof. Some embodiments comprise a recombinant vaccine that encodes the amino acid sequence for a consensus immunogen selected from the group consisting of HPV 6 E6 and E7, HPV 11 E6 and E7, HPV 33 E6 and E7, HPV 58 E6 and E7, and fragments thereof. Some embodiments comprise a subunit vaccine that comprises the amino acid sequence for a consensus immunogen selected from the group consisting of HPV 6 E6 and E7, HPV 11 E6 and E7, HPV 33 E6 and E7, HPV 58 E6 and E7, and fragments thereof. Some embodiments comprise a live attenuated vaccine and/or a killed vaccine that comprise the amino acid sequence for a consensus immunogen selected from the group consisting of HPV 6 E6 and E7, HPV 11 E6 and E7, HPV 33 E6 and E7, and HPV 58 E6 and E7.

In one aspect, the vaccines herein are those that elicit an immune response against HPV subtypes found predominantly to be associated with forms of head and neck cancer, and other forms of otolaryngologic diseases, in particular the vaccines include HPV 6 E6 and E7 and HPV 11 E6 and E7, and preferably both.

In another aspect, the vaccines herein are those the elicit an immune response against HPV subtypes found predominantly to be associated with forms of cervical cancer in patients ex-United States and more particularly patients in Asia, in particular the vaccines include HPV 33 E6 and E7 and HPV 58 E6 and E7, and preferably both.

Improved vaccines comprise proteins and genetic constructs that encode proteins with epitopes that make them particularly effective as immunogens against which anti-HPV immune responses can be induced. Accordingly, vaccines can be provided to induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

Aspects of the invention provide methods of delivering the coding sequences of the protein on nucleic acid molecule such as plasmid, as part of recombinant vaccines and as part of attenuated vaccines, as isolated proteins or proteins part of a vector.

According to some aspects of the present invention, compositions and methods are provided which prophylactically and/or therapeutically immunize an individual DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

The present invention relates to improved attenuated live vaccines, improved killed vaccines and improved vaccines that use recombinant vectors to deliver foreign genes that encode antigens and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993;

5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

When taken up by a cell, the genetic construct(s) may remain present in the cell as a. functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode protein of the invention, and, additionally, genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GLyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided in which the coding sequences for the proteins described herein are linked to IgE signal peptide. In some embodiments, proteins described herein are linked to IgE signal peptide.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well known expression systems. For example, the commercially available plasmid pSE420 (Invitrogen, San Diego, Calif.) may be used for production of protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, electroporation methods and devices, traditional syringes, needleless injection devices, or "microprojectile bombardment gone guns".

Examples of electroporation devices and electroporation methods preferred for facilitating delivery of the DNA vaccines, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

The following is an example of an embodiment using electroporation technology, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The use of electroporation technology to deliver the improved HPV vaccine is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 μs, 20 μs, 10 μs or 1 μs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021, 579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as a-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalane and squalene, and hyaluronic acid may also be used administered in conjunction with the genetic construct In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses are provided. The vaccine may be a protein based, live attenuated vaccine, a cell vaccine, a recombinant vaccine or a nucleic acid or DNA vaccine. In some embodiments, methods of inducing an immune response in individuals against an immunogen, including methods of inducing mucosal immune responses, comprise administering to the individual one or more of CTACK protein, TECK protein, MEC protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine. The one or more of CTACK protein, TECK protein, MEC protein and functional fragments thereof may be administered prior to, simultaneously with or after administration of the isolated nucleic acid molecule that encodes an immunogen; and/or recombinant vaccine that encodes an immunogen and/or subunit vaccine that comprises an immunogen and/or live attenuated vaccine and/or killed vaccine. In some embodiments, an isolated nucleic acid molecule that encodes one or more proteins of selected from the group consisting of: CTACK, TECK, MEC and functional fragments thereof is administered to the individual.

The present invention is further illustrated in the following Example. It should be understood that this Example, while indicating embodiments of the invention, is given by way of illustration only. From the above discussion and this Example, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Each of the U.S. patents, U.S. applications, and references cited throughout this disclosure are hereby incorporated in their entirety by reference.

EXAMPLE

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

HPV6 and HPV11 E6/E7 Vaccine Design and Expression

Construction of HPV6 and 11 E6/E7 Consensus-Based Fusion Immunogens

The HPV type 6 or 11 E6 and E7 gene sequences were collected from GeneBank, and the consensus E6 and E7 nucleotide sequences were obtained after performing multiple alignment. The consensus sequence of HPV 6 E6 or E7 proteins was generated from 98 or 20 sequences, respectively, while the consensus sequence of HPV 11 E6 or E7 proteins was generated from 76 or 13 sequences, respectively. The multiple alignment procedure applied in the phylogenetic study included the application of Clustal X (version 2.0). As indicated in FIGS. 1A and B, there were about 0-2% of sequence divergence among the HPV strains belonging to the same type in their E6 and E7 proteins. However, the genetic distances could go up to 19.3% in the E6 protein and 16.3% in the E7 protein between HPV 6 and 11. Based on these results from the phylogenic analyses, we developed two type-specific E6/E7 consensus DNA vaccines.

Several modifications were conducted after generating the consensus E6/E7 fusion sequence (FIG. 1C). A highly efficient leader sequence was fused in frame upstream of the start codon to facilitate the expression. The codon and RNA optimization was also performed as described previously (J. Yan, et al., Cellular immunity induced by a novel HPV18 DNA vaccine encoding an E6/E7 fusion consensus protein in mice and rhesus macaques, Vaccine. 26 (2008) 5210-5215; and J. Yan, et al., Induction of antitumor immunity in vivo following delivery of a novel HPV-16 DNA vaccine encoding an E6/E7 fusion antigen, Vaccine. 27 (2009) 431-440). An endoproteolytic cleavage site was introduced between E6 and E7 protein for proper protein folding and better CTL processing. Both synthetic engineered 6E6E7 gene and 11E6E7 genes were 840 bp in length. The sequence verified synthetic genes were subcloned into the pVAX expression vector at the BamHI and XhoI sites respectively for further study. The consensus amino acid sequences were obtained by translating the consensus nucleotide sequences.

After obtaining HPV 6 and 11 consensus E6 and E7 sequences, condon optimization and RNA optimization was performed as previously described (J. Yan, et al., Vaccine. 26 (2008) 5210-5215; and J. Yan, et al., Induction, Vaccine. 27 (2009) 431-440). The fusion genes encoding either HPV type 6 or 11 consensus E6/E7 fusion protein (6E6E7 or 11E6E7) were synthesized and sequence verified. The synthesized 6E6E7 or 11E6E7 was digested with BamHI and XhoI, cloned into the expression vector pVAX (Invitrogen) under the control of the cytomegalovirus immediate-early promoter and these constructs were named as p6E6E7 or p11E6E7.

293-T cells were cultured in 6-well plates and transfected with pVAX, p6E6E7, or p11E6E7 using FuGENE6 Transfection Reagent (Roche Applied Science, Indianapolis, Ind.). Two days after transfection, the cells were lysed using Modified RIPA Cell Lysis Buffer and cell lysate was collected. The Western blot analyses were performed with an anti-HA monoclonal antibody (Sigma-Aldrich, St. Louis, Mo.) and visualized with horseradish peroxidase-conjugated goat anti-mouse IgG (Sigma-Aldrich, St Louis, Mo.) using an ECL™ Western blot analysis system (Amersham, Piscataway, N.J.).

Indirect immunofluorescent assays were performed using human rhabdomyosarcoma cells (RD cells) to verify expression of p6E6E7 and p11E6E7. RD cells cultured in chamber slides were transfected with pVAX, p6E6E7, or p11E6E7 using Turbofectin 8.0 (Origene, Rockville, Md.). Afterwards, the cells were fixed with PFA and permeabilized with 0.1% Triton-X in PBS. The cells were subjected to 1-2 hour incubations with primary and secondary antibodies in addition to washes of PBS supplemented with Glycine and BSA in between incubations. The primary and secondary antibodies used were monoclonal mouse anti-HA (Sigma-Aldrich, St. Louis, Mo.) and FITC-conjugated anti-mouse IgG (Abcam, Cambridge, Mass.), respectively. Hoechst staining was also performed to identify cell nuclei and localize the RD cells. After all incubations were completed, the cells were mounted with a glass slide fixed with Fluoromount-G (Southern Biotech, Birmingham, Ala.). The samples were viewed and imaged using a confocal microscope (CDB Microscopy Core, University of Pennsylvania Cell and Developmental Biology, Philadelphia, Pa.).

Example 2

Mice and Treatment Groups Vaccinations

Female C57BL/6 mice between 6 to 8 weeks old were used in this experiment. Mice were obtained from the Jackson Laboratory (Bar Harbor, Me.). The mice were housed and maintained by the University Laboratory Animal Resources at the University of Pennsylvania (Philadelphia, Pa.) in observance with the policies of the National Institutes of Health and the University of Pennsylvania Institutional Animal Care and Use Committee (IACUC). The mice used in these experiments were separated into groups of four for immunization. Mice were immunized with p6E6E7, p11E6E7, or both constructs and pVAX group served as negative control.

DNA Vaccination and Electroporation

Each mouse received three doses of 20 µg of each DNA plasmid at 14-day intervals. Mice in the group receiving both p6E6E7 and p11E6E7 received 20 µg of both plasmids for a total of 40 µg of DNA per vaccination. The DNA constructs were administered via intramuscular injection of the right quadriceps muscle, followed by square-wave pulses generated by the CELLECTRA™ electroporator (Inovio Pharmaceuticals, Blue Bell, Pa.). The electroporator was configured to deliver two electric pulses at 0.2 Amps at 52 ms/pulse spaced apart by a 1 second delay. Electroporation procedure was performed as described previously [12,13].

IFN-γ ELISpot Assay

Mice in both treatment and control groups were sacrificed 1 week after the third immunization. Spleens were harvested from each mouse and transferred to RPMI-1640 medium with 10% FBS and antibiotics (R10). Using a stomacher (Seward Laboratory Systems, Bohemia, N.Y.), the spleens were pulverized and subsequently transferred through a cell strainer and suspended in ACK lysing buffer. After removing erythrocytes, the splenocytes were isolated and suspended in R10 medium. High-protein IP 96-well Multiscreen™ plates (Millipore, Bedford, Mass.) were pre-coated with monoclonal mouse IFN-γ Capture Antibody (R&D Systems, Minneapolis, Minn.) and incubated overnight at 4° C. After three washes with 1×PBS, the plates were blocked with 1% BSA and 5% sucrose in 1×PBS for 2 hours at ambient temperature. Isolated splenocytes in R10 medium were counted and added in triplicate wells at 2×10⁵ cells per well. Two sets of peptides spanning the consensus E6/E7 sequence for HPV6 and HPV11 were reconstituted in DMSO (GenScript USA, Piscataway, N.J.). The peptides contained 15 amino acid sequences, of which 8 residues overlapped with each sequential peptide. The peptides for HPV6 and 11 were each divided into two pools—one pool for E6 and another for E7—at concentrations of 2 μg/mL in DMSO. Wells reserved for positive and negative control received Concavalin A (Sigma-Aldrich, St. Louis, Mo.) and R10 culture medium in lieu of peptides, respectively. Plates were subsequently placed in a 5% CO2 atmosphere incubator. After incubation for 24 hours at 37° C., the wells were washed with 1×PBS. Biotinylated anti-mouse IFN-γ Detection Antibody (R&D Systems, Minneapolis, Minn.) was added to each well and then incubated overnight at 4° C. The plates were subsequently washed and processed per a color development protocol provided by R&D Systems using Streptavidin-AP and BCIP/NBT Plus (R&D Systems, Minneapolis, Minn.). The wells were air-dried overnight and spots inside wells were scanned and counted by an ELISpot plate reader system with Immuno-Spot®3 and ImmunoSpot®4 software (Cellular Technology Ltd., Shaker Heights, Ohio). Reported spot-forming cell counts were converted to represent spot-forming units per 1×106 splenocytes using arithmetic.

Given their sensitivity and ability to illustrate T-cell activity, IFN-γ ELISpot assays were used to determine the number of antigen-specific IFN-gamma secreting cells in response to stimulation with either HPV 6 or 11 E6 and E7 peptides.

Figure 3A:
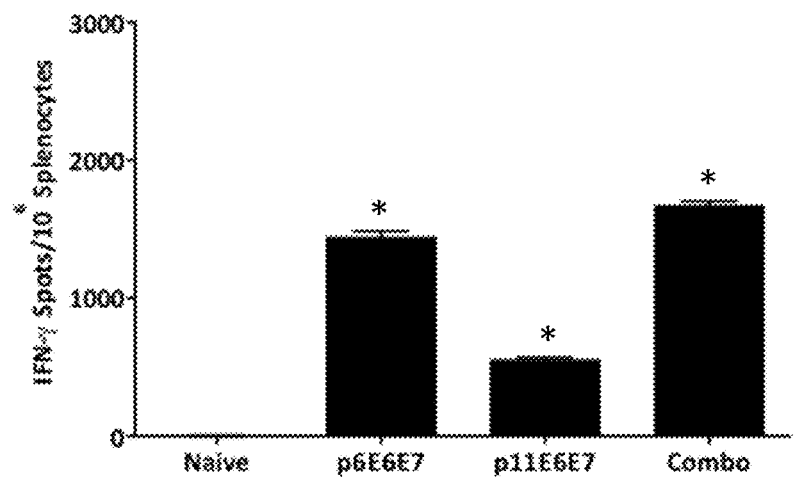
FIG. 3. IFN-γ ELISpot assays show induction of robust cell-mediated responses by p6E6E7 (A) and p11E6E7 (B) in C57BL/6 mice. Assays were performed using splenocytes isolated from mice in each respective group (5 mice per group) after three biweekly immunizations. Each immunization consisted of 20 µg per construct. Mice in combo group received both p6E6E7 and p11E6E7 at 20 µg per construct, for a total of 40 µg DNA per immunization. DNA was administered via IM injection, followed by electroporation (* denotes p<0.0001; † denotes p=0.0001).
Figure 3B:
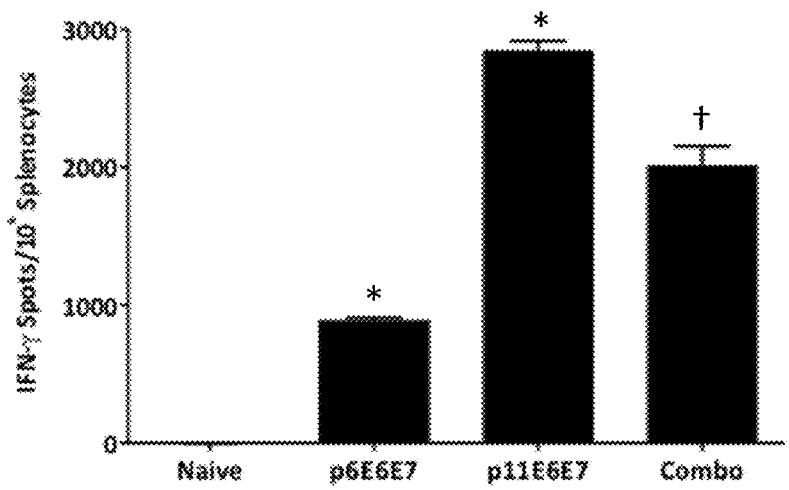

As shown in FIGS. 3A and 3B, the average number of SFU/106 splenocytes for mice vaccinated with p6E6E7 was 1442.8, while the average number of SFU/106 for mice immunized with p11E6E7 was 2845, which were all significantly greater than the negative control group. Therefore, both p6E6E7 and p11E6E7 were effective in eliciting robust type-specific E6 and E7-specific immune response in mice.

Interestingly, the cross-reactive cellular immune responses were also induced by vaccination with p6E6E7 or p11E6E7. The additive frequency of SFU/106 splenocytes in p11E6E7 immunized mice against HPV 6 E6/E7 peptides was 552.8 SFU/106 splenocytes, and the HPV 11 E6/E7-specific immune responses in p6E6E7 immunized mice was 888.3 SFU/106 splenocytes. The E6 proteins of HPV 6 or 11 share about 80% identity, while the E7 proteins of HPV6 or 11 shared about 84% identity. There may be some shared immune epitopes between HPV 6 or 11 E6 and E7 antigens. The cross-reactivity observed from the IFN-gamma ELISpot assay indicated that there were shared immune epitopes between HPV6 and 11 E6 and E7 antigens.

Splenocytes from mice that received both p6E6E7 and p11E6E7 (combo group) were also subjected to the above ELISpot assays in order to examine whether there was any immune interference when these two constructs were vaccinated together (FIGS. 3A and B). The combo group exhibited an average of 1670 SFU/106 splenocytes (σ=55.7, p<0.001) against HPV6 E6 and E7 peptides. The same group of splenocytes produced 2010 SFU/106 splenocytes (σ=247.8, p=0.002) against HPV11 E6 and E7 peptides. The data suggest that concurrent vaccination with the two constructs can elicit a statistically significant E6 and E7-specific cellular response against HPV6 and HPV 11 and that these responses do not interfere with each other.

Epitope Mapping

Figure 4A:
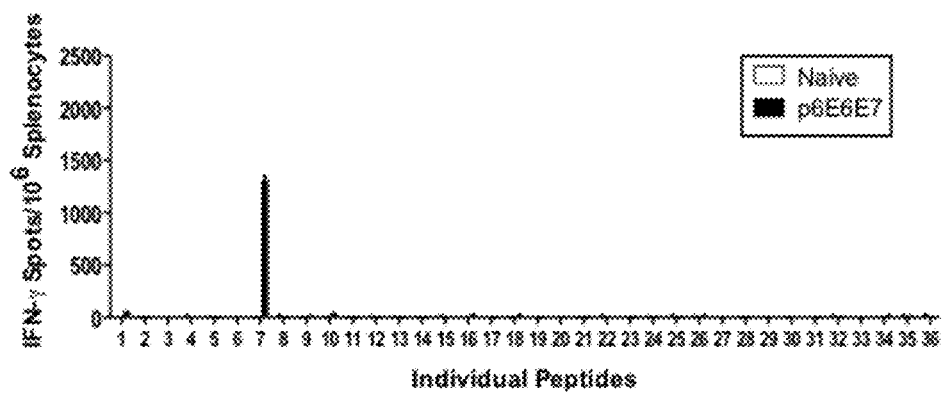
FIG. 4. Additional IFN-γ ELISpot assays performed using individual peptides to characterize dominant epitopes. Splenocytes isolated from vaccinated mice and negative control were stimulated with overlapping peptides that span the entire HPV 6 E6/E7 fusion protein (A) or HPV 11 E6/E7 fusion protein (B).
Figure 4B:
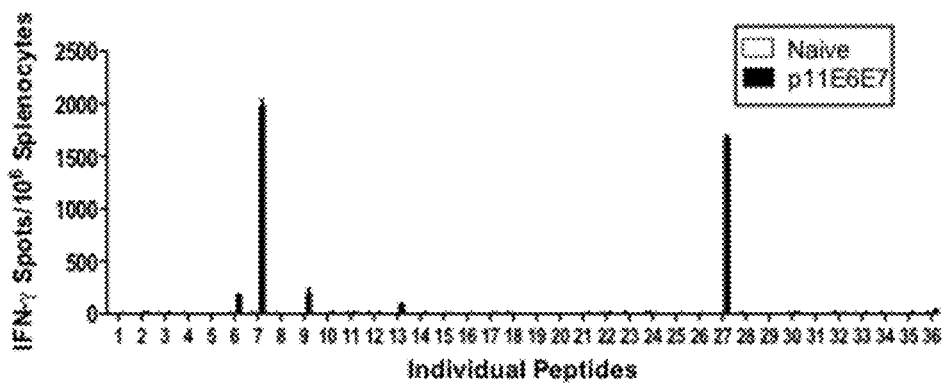

Epitope mapping studies were performed to determine dominant epitopes within peptide pools, in order to determine the immune dominant peptides within the E6/E7 consensus antigens (FIGS. 4A and 4B). The studies were performed similarly to the previously mentioned IFN-γ ELISpot assay. Instead of pools, individual peptides were used to stimulate the splenocytes.

Each peptide used in this single-peptide analysis represented a partially overlapping fragment of the E6 and E7 antigens of HPV6 or HPV 11. The mapping data indicated that peptide 7 (TAEIYSYAYKQLKVL) SEQ ID NO:11 was the dominant epitope for the HPV6 E6 and E7 immunogens (FIG. 4A). TAEIYSYAYKQLKVL SEQ ID NO:11 contained 8, 9, 10-mer amino acid epitopes that are verified to be an H2-Kb restricted by the HLA-binding prediction software made available by NIH BIMAS. To further describe the HPV11 E6 and E7-specific T-cell immune response (FIG. 4B). Peptide analysis was also performed with overlapping fragments of HPV11 E6 and E7. Epitope mapping showed that the dominant epitopes for HPV 11 E6 and E7 antigens were peptides 7 (TAEIYAYAYKNLKVV) SEQ ID NO:12 and 27 (HCYEQLEDSSEDEVD) SEQ ID NO:13. As with peptide 7 in the HPV6 epitope mapping assay, the BIMAS HLA-binding prediction software confirmed TAEIYAYAYKNLKVV SEQ ID NO:12 to be an H2-Kb restricted epitope. Another HLA-binding peptide database, the Immune Epitope Database and Analysis Resource provided by NIH NIAID, confirmed that HCYEQLEDSSEDEVD SEQ ID NO:13 is an H2-Kb restricted epitope. Three immune subdominant peptides, numbers 6 (FCKNALTTAEIYSYA) SEQ ID NO:14, 9 (LFRGGYPYAACACCL) SEQ ID NO:15, and 13 (YAGYATTVEEETKQD) SEQ ID NO:16, were identified through this epitope mapping study.

Intracellular Cytokine Staining

In light of the high immune response portrayed by the IFN-γ ELISpot assays, intracellular cytokine staining assays were performed to provide a more holistic overview of the cellular response induced by p6E6E7 and p11E6E7. Splenocytes from vaccinated and naive mouse groups were isolated and stimulated with peptides spanning the E6 and E7 regions of HPV6 and HPV11 for 4 hours at 37° C. in a 5% CO2 environment. Positive and negative controls were used in the assay by placing cells in phorbol 12-myristate 13-acetate (PMA) and R10 cell media, respectively. After incubation, the cells were first stained with ViViD Dye (Invitrogen, Carlsbad, Calif.) to differentiate between live and dead cells, then all cells were stained with the following surface marker antibodies: APC-Cy7 Hamster anti-Mouse CD3e, PerCP-Cy5.5 Rat anti-Mouse CD4, and APC Rat anti-Mouse CD8a (BD Biosciences, San Diego, Calif.). The cells were subsequently fixed using the Cytofix/Cytoperm kit (BD Biosciences, San Diego, Calif.). After fixation per manufacturer protocol, the cells were stained with the following intracellular marker antibodies: Alexa Fluor 700 Rat anti-Mouse IFN-γ, PE-Cy7 Rat anti-Mouse TNF Clone, and PE Rat anti-Mouse IL-2 (BD Biosciences, San Diego, Calif.). After staining, the cells were fixed with a solution of PBS containing 2% paraformaldehyde. The prepared cells were acquired using an LSR II flow cytometer equipped with BD FACSDiva software (BD Biosciences, San Jose, Calif.). Acquired data was analyzed using the latest version of FlowJo software (Tree Star, Ashland, Oreg.). CD4+ and CD8+ events were isolated using the following sequence of gates: singlet from FSC-A vs FSC-H, all splenocytes from FSC-A vs SSC-A, live cells from ViViD Dye (Pacific Blue) vs SSC-A, CD3+ cells from CD3 (APC-Cy7) vs SSC-A, and CD4+ or CD8+ from CD4 (PerCP-Cy5.5: positive—CD4+, negative—CD8+) vs SSC-A. The last two populations were gated against Alexa Fluor 700, PE-Cy7, and PE to observe changes in IL-2, IFN-γ, and TNF-α production, respectively.

Figure 5A:
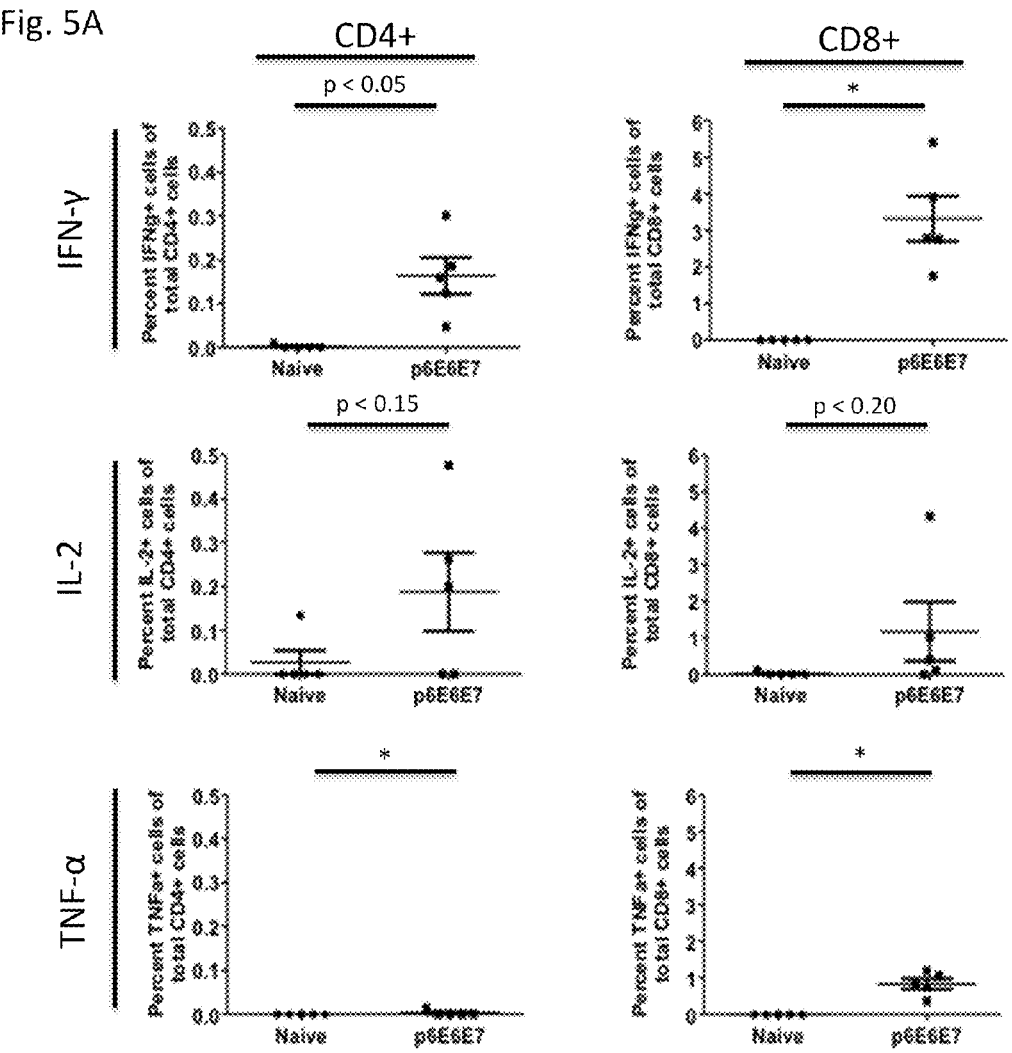
FIG. 5. Cytokine production by antigen-specific T-cells characterized by intracellular cytokine staining. Splenocytes isolated from mice vaccinated with p6E6E7 (A) and p11E6E7 (B) were stimulated with R10 growth medium, PMA, or consensus gene peptides for 4 hours prior to surface marker and intracellular staining. Dot plots above show differences in background-subtracted percentages of either total CD4+ or CD8+ cells producing IFN-γ, IL-2, and TNF-α. P-values for plots with asterisks were unable to be determined because the average of the negative control group was zero.
Figure 5B:
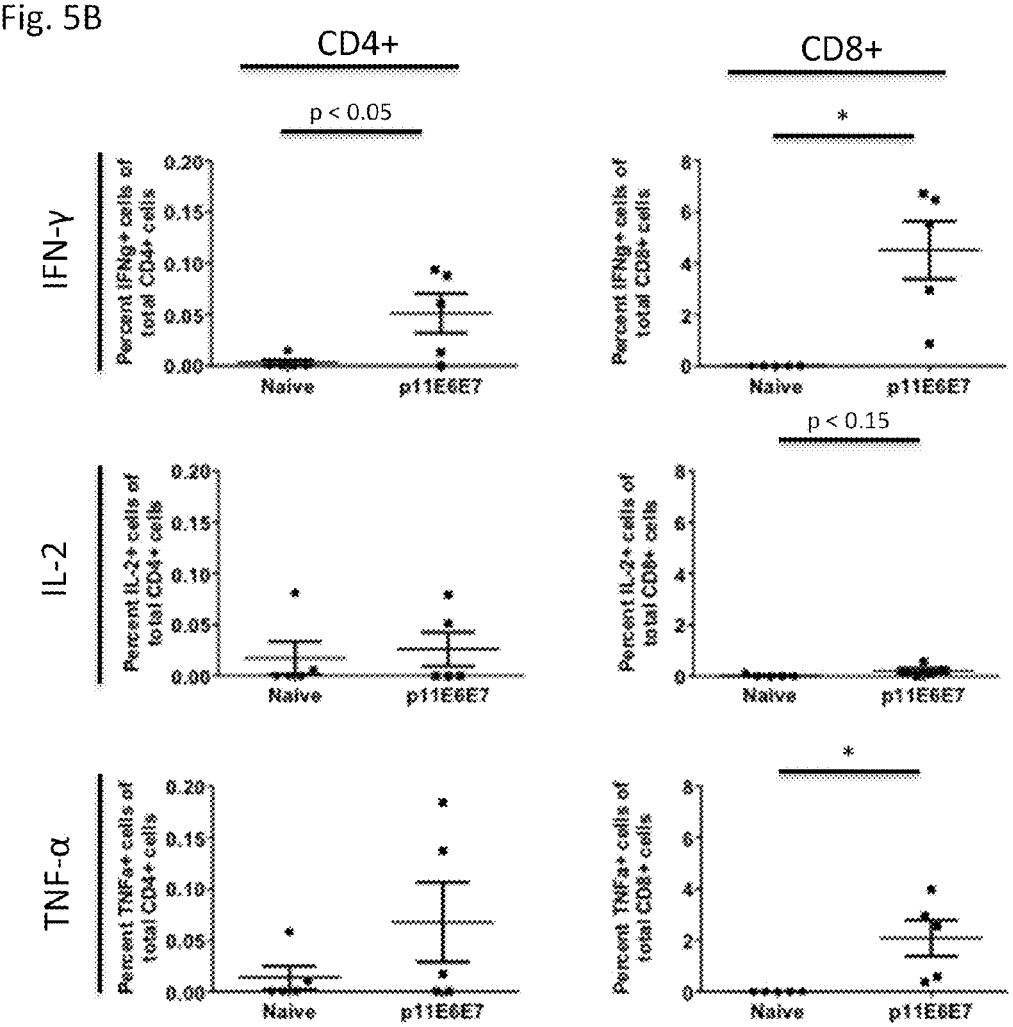

Cells were gated such that intracellular cytokine staining data can differentiate by CD4+ and CD8+ cell responses. When stimulated with HPV6 E6 and E7-specific peptides, mice vaccinated with p6E6E7 exhibited averages of 0.163% (σ=0.09), 0.003% (σ=0.07), and 0.188% (σ=0.20) of total CD4+ cells producing IFN-γ, TNF-α, and IL-2, respectively (FIG. 5A). The same group of mice had averages of 3.323% (σ=1.39), 0.838% (σ=0.32), and 1.172% (σ=1.81) of total CD8+ cells producing IFN-γ, TNF-α, and IL-2, respectively. The same intracellular cytokine data was collected using splenocytes from mice vaccinated with p11E6E7 after incubation with HPV11 E6 and E7 antigens (FIG. 5B). Of all CD4+ cells in the p11E6E7 vaccinated mice, an average of 0.051% (σ=0.04) produced IFN-γ, 0.068% (σ=0.09) produced TNF-α, and 0.026% (σ=0.037) produced IL-2. Further, an average of 4.52% (σ=2.53), 2.08% (σ=1.56), and 0.21% (σ=0.22) of all CD8+ cells in p11E6E7 vaccinated mice produced IFN-γ, TNF-α, and IL-2, respectively. With the exception of a few panels, the percentage of cytokine producing cells in treatment versus their respective naïve groups was statistically significant at a confidence level of 89% or higher. Observation of the magnitude of cytokine production of CD4+ cells versus CD8+ T-cells, one can conclude that the immune responses elicited by p6E6E7 and p11E6E7 is heavily skewed towards driving CD8+ lymphocytes, which are associated in all models with their cell clearance.

Statistical Analysis

Student's t tests were performed to analyze statistical significance of all quantitative data produced in this study. Unless otherwise indicated, p-values were calculated to determine statistical significance at various confidence levels. This study has shown compelling evidence that DNA vaccines may be able to attain a level of immunogenicity found in experiments using other popular and traditional vaccine platforms. High levels of cellular responses measured in other similar E6 and E7-specific HPV DNA vaccine studies were associated with data suggestive of prophylactic and therapeutic anti-tumor efficacy. Most HPV-related research and disease challenge models focus on cervical cancer. Given that HPV6 and HPV11 are not as relevant to cervical cancer as other HPV serotypes, the therapeutic efficacy of p6E6E7 and p11E6E7 cannot be fully evaluated using conventional HPV disease challenge models. It would be insightful to determine the protective and therapeutic potential of p6E6E7 and p11E6E7 when appropriate disease challenge models become available. Thus, one can only infer the immunogenic efficacy of p6E6E7 and p11E6E7 by looking at the high levels of IFN-γ and cytokine production quantified by the ELISpot assays and intracellular cytokine staining Nonetheless, such levels were found to be significantly robust in magnitude and show promise that the two constructs would elicit substantive levels of cellular immune responses. Because HPV-related malignancies are generally secondary to concurrent infection of multiple serotypes, there is a great need to look further into the feasibility of combining vaccines targeting different serotypes of the virus. Future study looking into T-cell dynamics and vaccine competition is warranted to further characterize the effects of concurrent vaccination of the two plasmids.

Intracellular cytokine staining showed that vaccination with p6E6E7 and p11E6E7 was able to elicit a significant percentage of IFN-γ, TNF-α, and IL-2 producing T-cells. Given its currently known function in the immune system, IFN-γ has historically been used as a metric of cellular immune responses. Some of these important roles include the ability to modulate and stimulate innate and adaptive immunity. Moreover, it is widely accepted that the principle producers of IFN-γ are T-cells, making IFN-γ production an acceptable mode of measuring the cellular immunogenicity of a given vaccine post-exposure to antigens. TNF-α is another cytokine that is involved in the regulation of the immune system. Its known ability to induce apoptosis and regulate tumor proliferation makes it an important parameter to consider when characterizing post-vaccination immune responses. TNF-α production may be of further interest given the potential tumor proliferative properties of HPV6 and HPV 11. IL-2 is another signaling molecule that has been observed to play a central role in the proliferation and differentiation of T-cells in the immune system. As a consequence, IL-2 is often examined in conjunction with other cytokines to gain further perspective on the magnitude and quality of a particular immune response. Given the above, the significant percentages of CD4+ and CD8+ cells producing IFN-γ, TNF-α, and IL-2 after vaccination with p6E6E7 suggests that the vaccine was successful in inducing a potent immune response. With the exception of IL-2 secreting CD4+ cells, the same trend is true for cells isolated from mice vaccinated with p11E6E7. Moreover, it is noteworthy to observe that CD8+ cells heavily drove the immune responses in vaccinated mice—a characteristic that is significant in evaluating the anti-tumor efficacy of the two plasmids.

The invention claimed is:

1. A nucleic acid molecule comprising a nucleotide sequence encoding for an HPV antigen, the nucleotide sequence selected from the group consisting of: SEQ ID NO: 1, SEQ ID NO: 3, SEQ ID NO: 5, SEQ ID NO: 7, a fragment having 90% sequence identity to SEQ ID NO: 1, a fragment having 90% sequence identity to SEQ ID NO: 3, a fragment having 90% sequence identity to SEQ ID NO: 5, a fragment having 90% sequence identity to SEQ ID NO: 7, and any combinations thereof.

2. The nucleic acid molecule of claim 1 comprising a nucleotide sequence selected from the group consisting of SEQ ID NO:1, SEQ ID NO:3, SEQ ID NO:5, SEQ ID NO:7, and any combinations thereof.

3. The nucleic acid molecule of claim 1 comprising a nucleotide sequence selected from the group consisting of a fragment having at least 95% sequence identity to SEQ ID NO: 1, a fragment having at least 95% sequence identity to SEQ ID NO: 3, a fragment having at least 95% sequence identity to SEQ ID NO: 5, and a fragment having at least 95% sequence identity to SEQ ID NO: 7.

4. The nucleic acid molecule of claim 1 comprising a nucleotide sequence selected from the group consisting of a fragment having at least 98% sequence identity to SEQ ID NO: 1, a fragment having at least 98% sequence identity to SEQ ID NO: 3, a fragment having at least 98% sequence identity to SEQ ID NO: 5, and a fragment having at least 98% sequence identity to SEQ ID NO: 7.

5. The nucleic acid molecule of claim 1 comprising a nucleotide sequence selected from the group consisting of a fragment of the nucleotide sequence having at least 99% sequence identity to SEQ ID NO: 1, a fragment having at least 99% sequence identity to SEQ ID NO:3, a fragment having at least 99% sequence identity to SEQ ID NO:5, and a fragment having at least 99% sequence identity to SEQ ID NO:7.

6. A nucleic acid molecule comprising a nucleotide sequence selected from the group consisting of: a nucleotide sequence that encodes an amino acid sequence selected from the group consisting of SEQ ID NO: 2, SEQ ID NO:4, SEQ ID NO:6, SEQ ID NO:8, a nucleotide sequence that encodes an amino acid sequence fragment having at least 90% sequence identity to SEQ ID NO:2, a nucleotide sequence that encodes an amino acid fragment having at least 90% sequence identity to SEQ ID NO:4, a nucleotide sequence that encodes an amino acid fragment having at least 90% sequence identity to SEQ ID NO:6, and a nucleotide sequence that encodes an amino acid fragment having at least 90% sequence identity to SEQ ID NO:8.

7. The nucleic acid molecule of claim 6 comprising a nucleotide sequence that encodes SEQ ID NO:2, SEQ ID NO:4, SEQ ID NO:6, or SEQ ID NO:8.

8. The nucleic acid molecule of claim 6 wherein said molecule is a plasmid.

9. A pharmaceutical composition comprising a nucleic acid molecule of claim 6.

10. A method of inducing an immune response in an individual against HPV comprising administering to said individual a composition comprising a nucleic acid molecule of claim 1.

11. The method of claim 10, further comprising introducing said nucleic acid molecule into the individual by electroporation.

12. An immunogenic composition comprising a nucleic acid molecule of claim 1.

13. The immunogenic composition of claim 12 wherein said immunogenic composition is a recombinant immunogenic composition.

14. A protein comprising an amino acid sequence selected from the group consisting of: SEQ ID NO:2, SEQ ID NO:4, SEQ ID NO:6, SEQ ID NO:8, a fragment having at least 90% sequence identity to SEQ ID NO:2, a fragment having at least 90% sequence identity to SEQ ID NO:4, a fragment having at least 90% sequence identity to SEQ ID NO:6, and a fragment having at least 90% sequence identity to SEQ ID NO:8.

15. The protein of claim 14 comprising SEQ ID NO:2, SEQ ID NO:4, SEQ ID NO:6, or SEQ ID NO:8.

16. The protein of claim 14 comprising a fragment having at least 95% sequence identity to SEQ ID NO:2, a fragment having at least 95% sequence identity to SEQ ID NO:4, a fragment having at least 95% sequence identity to SEQ ID NO:6, or a fragment having at least 95% sequence identity to SEQ ID NO:8.

17. The protein of claim 14 comprising a fragment having at least 98% sequence identity to SEQ NO:2, a fragment having at least 98% sequence identity to SEQ ID NO:4, a fragment having at least 98% sequence identity to SEQ ID NO:6, or a fragment having at least 98% sequence identity to SEQ ID NO:8.

18. The protein of claim 14 comprising a fragment having at least 99% sequence identity to SEQ ID NO: 2, a fragment having at least 99% sequence identity to SEQ ID NO: 4, a fragment having at least 99% sequence identity to SEQ ID NO: 6, or a fragment having at least 99% sequence identity to SEQ ID NO: 8.

19. A method of inducing an immune response in an individual against HPV comprising administering to said individual the immunogenic composition of claim 12.

20. The method of claim 10, further comprising diagnosing the individuals having HPV infection.

21. A pharmaceutical composition comprising a nucleotide sequence encoding for an HPV antigen, wherein the nucleotide sequence is selected from a group consisting of SEQ ID NO: 1, SEQ ID NO: 3, a fragment having 90% identity to SEQ ID NO: 1, and a fragment having 90% identity to SEQ ID NO: 3.

22. A method of inducing an immune response in an individual against HPV subtypes 6 or 11 comprising administering to said individual the pharmaceutical composition of claim 21.

23. A pharmaceutical composition comprising a nucleotide sequence encoding for an HPV antigen, wherein the nucleotide sequence is selected from a group consisting of SEQ ID NO: 5, SEQ ID NO: 7, a fragment having 90% identity to SEQ ID NO: 5, and a fragment having 90% identity to SEQ ID NO: 7.

24. A method of inducing an immune response in an individual against HPV subtypes 33 or 58 comprising administering to said individual the pharmaceutical composition of claim 23.

* * * * *

SEQUENCE LISTING

```
<160> NUMBER OF SEQ ID NOS: 16

<210> SEQ ID NO 1
<211> LENGTH: 873
<212> TYPE: DNA
<213> ORGANISM: Artificial Sequence
<220> FEATURE:
<223> OTHER INFORMATION: HPV6 E6E7 DNA sequence

<400> SEQUENCE: 1
ggtaccggat ccgccaccat ggactggacc tggattctgt tcctggtggc cgctgccaca      60
cgggtgcaca gcgaaagcgc caatgccagc accagcgcta caaccatcga ccagctgtgc     120
aagaccttca acctgagcat gcacaccctg cagatcaact gcgtgttctg caagaacgcc     180
ctgaccaccg ccgagatcta cagctacgcc tacaagcagc tgaaggtgct gttcagaggc     240
ggctacccct atgccgcctg cgcctgctgc ctggaatttc acggcaagat caaccagtac     300
cggcacttcg actacgccgg ctacgccacc accgtggaag aggaaacaaa gcaggacatc     360
```

```
ctggacgtgc tgatccggtg ctacctgtgc cacaagcccc tgtgcgaggt ggaaaaagtg      420
aagcacatcc tgaccaaggc ccggttcatc aagctgaact gcacctggaa gggccggtgc      480
ctgcactgct ggaccacctg tatggaagat atgctgccca gaggccggaa gcggcggagc      540
catggcagac acgtgaccct gaaggacatc gtgctggacc tgcagccccc cgatcctgtg      600
ggcctgcact gttacgagca gctggtggac agcagcgagg acgaggtgga cgaagtggac      660
ggccaggaca gccagcccct gaagcagcac ttccagatcg tgacctgctg ctgcggctgc      720
gacagcaacg tgcggctggt ggtgcagtgc accgagacag acatcagaga ggtccagcag      780
ctcctgctgg gcaccctgaa catcgtgtgc cccatctgcg cccccaagac ctacccttac      840
gacgtgcccg actacgcctg atgactcgag ctc                                   873
```

<210> SEQ ID NO 2
<211> LENGTH: 280
<212> TYPE: PRT
<213> ORGANISM: Artificial Sequence
<220> FEATURE:
<223> OTHER INFORMATION: HPV6 E6E7 protein sequence

<400> SEQUENCE: 2

```
Met Asp Trp Thr Trp Ile Leu Phe Leu Val Ala Ala Ala Thr Arg Val
 1               5                  10                  15

His Ser Glu Ser Ala Asn Ala Ser Thr Ser Ala Thr Thr Ile Asp Gln
            20                  25                  30

Leu Cys Lys Thr Phe Asn Leu Ser Met His Thr Leu Gln Ile Asn Cys
        35                  40                  45

Val Phe Cys Lys Asn Ala Leu Thr Thr Ala Glu Ile Tyr Ser Tyr Ala
    50                  55                  60

Tyr Lys Gln Leu Lys Val Leu Phe Arg Gly Gly Tyr Pro Tyr Ala Ala
65                  70                  75                  80

Cys Ala Cys Cys Leu Glu Phe His Gly Lys Ile Asn Gln Tyr Arg His
                85                  90                  95

Phe Asp Tyr Ala Gly Tyr Ala Thr Thr Val Glu Glu Glu Thr Lys Gln
           100                 105                 110

Asp Ile Leu Asp Val Leu Ile Arg Cys Tyr Leu Cys His Lys Pro Leu
       115                 120                 125

Cys Glu Val Glu Lys Val Lys His Ile Leu Thr Lys Ala Arg Phe Ile
   130                 135                 140

Lys Leu Asn Cys Thr Trp Lys Gly Arg Cys Leu His Cys Trp Thr Thr
145                 150                 155                 160

Cys Met Glu Asp Met Leu Pro Arg Gly Arg Lys Arg Arg Ser His Gly
                165                 170                 175

Arg His Val Thr Leu Lys Asp Ile Val Leu Asp Leu Gln Pro Pro Asp
            180                 185                 190

Pro Val Gly Leu His Cys Tyr Glu Gln Leu Val Asp Ser Ser Glu Asp
        195                 200                 205

Glu Val Asp Glu Val Asp Gly Gln Asp Ser Gln Pro Leu Lys Gln His
    210                 215                 220

Phe Gln Ile Val Thr Cys Cys Cys Gly Cys Asp Ser Asn Val Arg Leu
225                 230                 235                 240

Val Val Gln Cys Thr Glu Thr Asp Ile Arg Glu Val Gln Gln Leu Leu
                245                 250                 255

Leu Gly Thr Leu Asn Ile Val Cys Pro Ile Cys Ala Pro Lys Thr Tyr
            260                 265                 270
```

Pro Tyr Asp Val Pro Asp Tyr Ala
            275                 280

<210> SEQ ID NO 3
<211> LENGTH: 873
<212> TYPE: DNA
<213> ORGANISM: Artificial Sequence
<220> FEATURE:
<223> OTHER INFORMATION: HPV11 E6E7 DNA sequence

<400> SEQUENCE: 3

```
ggtaccggat ccgccaccat ggactggacc tggattctgt tcctggtggc cgctgccaca    60
agagtgcaca gcgagagcaa ggatgccagc accagcgcca ccagcatcga ccagctgtgc   120
aagaccttca acctgagcct gcacaccctg cagatccagt gcgtgttctg ccggaacgcc   180
ctgaccaccg ccgagatcta cgcctacgcc tacaagaacc tgaaggtcgt gtggcgggac   240
aacttcccct tcgccgcctg cgcctgctgc ctggaactgc agggcaagat caaccagtac   300
cggcacttca actacgccgc ttacgccccc accgtggaag aggaaacaaa cgaggacatc   360
ctgaaggtgc tgatccggtg ctacctgtgc cacaagcccc tgtgcgagat cgagaagctg   420
aagcacatcc tgggcaaggc ccggttcatc aagctgaaca ccagtggaa gggccggtgc    480
ctgcactgct ggaccacctg tatggaagat ctgctgccca gaggccggaa gcggagaagc   540
cacggcagac tggtcaccct gaaggacatc gtgctggacc tgcagccccc cgatcctgtg   600
ggcctgcact gttacgagca gctggaagat agcagcgagg acgaggtgga caaagtggac   660
aagcaggacg cccagcccct gacccagcac taccagatcc tgacctgctg ctgcggctgc   720
gacagcaacg tgcggctggt ggtggaatgc accgacggcg acatccggca gctccaggat   780
ctgctgctgg gcaccctgaa catcgtgtgc cccatctgcg ccccaagcc ctaccccctac  840
gacgtgcccg actacgcctg atgactcgag ctc                                873
```

<210> SEQ ID NO 4
<211> LENGTH: 280
<212> TYPE: PRT
<213> ORGANISM: Artificial Sequence
<220> FEATURE:
<223> OTHER INFORMATION: HPV11 E6E7 protein sequence

<400> SEQUENCE: 4

Met Asp Trp Thr Trp Ile Leu Phe Leu Val Ala Ala Thr Arg Val
1               5                   10                  15

His Ser Glu Ser Lys Asp Ala Ser Thr Ser Ala Thr Ser Ile Asp Gln
            20                  25                  30

Leu Cys Lys Thr Phe Asn Leu Ser Leu His Thr Leu Gln Ile Gln Cys
        35                  40                  45

Val Phe Cys Arg Asn Ala Leu Thr Thr Ala Glu Ile Tyr Ala Tyr Ala
    50                  55                  60

Tyr Lys Asn Leu Lys Val Val Trp Arg Asp Asn Phe Pro Phe Ala Ala
65                  70                  75                  80

Cys Ala Cys Cys Leu Glu Leu Gln Gly Lys Ile Asn Gln Tyr Arg His
                85                  90                  95

Phe Asn Tyr Ala Ala Tyr Ala Pro Thr Val Glu Glu Thr Asn Glu
            100                 105                 110

Asp Ile Leu Lys Val Leu Ile Arg Cys Tyr Leu Cys His Lys Pro Leu
        115                 120                 125

Cys Glu Ile Glu Lys Leu Lys His Ile Leu Gly Lys Ala Arg Phe Ile

```
                130                 135                 140
Lys Leu Asn Asn Gln Trp Lys Gly Arg Cys Leu His Cys Trp Thr Thr
145                 150                 155                 160

Cys Met Glu Asp Leu Leu Pro Arg Gly Arg Lys Arg Arg Ser His Gly
                165                 170                 175

Arg Leu Val Thr Leu Lys Asp Ile Val Leu Asp Leu Gln Pro Pro Asp
                180                 185                 190

Pro Val Gly Leu His Cys Tyr Glu Gln Leu Glu Asp Ser Ser Glu Asp
            195                 200                 205

Glu Val Asp Lys Val Asp Lys Gln Asp Ala Gln Pro Leu Thr Gln His
    210                 215                 220

Tyr Gln Ile Leu Thr Cys Cys Cys Gly Cys Asp Ser Asn Val Arg Leu
225                 230                 235                 240

Val Val Glu Cys Thr Asp Gly Asp Ile Arg Gln Leu Gln Asp Leu Leu
                245                 250                 255

Leu Gly Thr Leu Asn Ile Val Cys Pro Ile Cys Ala Pro Lys Pro Tyr
                260                 265                 270

Pro Tyr Asp Val Pro Asp Tyr Ala
            275                 280

<210> SEQ ID NO 5
<211> LENGTH: 828
<212> TYPE: DNA
<213> ORGANISM: Artificial Sequence
<220> FEATURE:
<223> OTHER INFORMATION: HPV33 E6E7 DNA sequence

<400> SEQUENCE: 5
ggtaccgtcg acggatccgc caccatggac tggacctgga ttctgttcct ggtggccgct      60
gctacccggg tgcacagctt ccaggacacc gaggaaagcg ccggaccct gcacgatctg     120
tgccaggccc tggaaaccac catccacaac atcgagctgc agtgcgtgga atgcaagaag     180
cccctgcagc ggagcgaggt gtacgacgcc gacctgaccg tggtgtacag agagggcaac     240
cccttcggca tctgcaagct gtgcctgcgg ttcctgagca agatcagcga gtaccggcac     300
tacaactaca gcgtgtacgg caacaccctg gaacagaccg tgaagaagcc tctgaacgag     360
atcctgatcc ggtgcatcat ctgccagcgg cccctgaagc ggcacgtgga cctgaacaag     420
cggttccaca tatcagcgg cagatgggcc ggcagatgcg ccgcctgttg agaagccgg     480
cggagagaga cagccctgcg gggcagaaag cggcggagca gaggccacaa gcccaccctg     540
aaagaatacg tgctggacct gtaccccgag cccaccgacc tgtacggcta cggccagctg     600
agcgacagca gcgacgagga cgagggcctg gacagacctg atggacaggc ccagcccgcc     660
accgccgact actacatcgt gacctgctgc cacacctgta acaccaccgt gcggctgtgc     720
gtgaacagca ccgccagcga cctgcggaca atccagcagc tcctgatggg caccgtgaac     780
atcgtgtgcc ctacctgcgc ccagctgtga ctcgagacgc gtgagctc                  828

<210> SEQ ID NO 6
<211> LENGTH: 261
<212> TYPE: PRT
<213> ORGANISM: Artificial Sequence
<220> FEATURE:
<223> OTHER INFORMATION: HPV33 E6E7 protein sequence

<400> SEQUENCE: 6

Met Asp Trp Thr Trp Ile Leu Phe Leu Val Ala Ala Thr Arg Val
1               5                   10                  15
```

```
His Ser Phe Gln Asp Thr Glu Glu Ser Gly Arg Thr Leu His Asp Leu
        20                  25                  30

Cys Gln Ala Leu Glu Thr Thr Ile His Asn Ile Glu Leu Gln Cys Val
            35                  40                  45

Glu Cys Lys Lys Pro Leu Gln Arg Ser Glu Val Tyr Asp Ala Asp Leu
 50                  55                  60

Thr Val Val Tyr Arg Glu Gly Asn Pro Phe Gly Ile Cys Lys Leu Cys
 65                  70                  75                  80

Leu Arg Phe Leu Ser Lys Ile Ser Glu Tyr Arg His Tyr Asn Tyr Ser
                85                  90                  95

Val Tyr Gly Asn Thr Leu Glu Gln Thr Val Lys Lys Pro Leu Asn Glu
            100                 105                 110

Ile Leu Ile Arg Cys Ile Ile Cys Gln Arg Pro Leu Lys Arg His Val
            115                 120                 125

Asp Leu Asn Lys Arg Phe His Asn Ile Ser Gly Arg Trp Ala Gly Arg
130                 135                 140

Cys Ala Ala Cys Trp Arg Ser Arg Arg Arg Glu Thr Ala Leu Arg Gly
145                 150                 155                 160

Arg Lys Arg Arg Ser Arg Gly His Lys Pro Thr Leu Lys Glu Tyr Val
                165                 170                 175

Leu Asp Leu Tyr Pro Glu Pro Thr Asp Leu Tyr Gly Tyr Gly Gln Leu
            180                 185                 190

Ser Asp Ser Ser Asp Glu Asp Glu Gly Leu Asp Arg Pro Asp Gly Gln
            195                 200                 205

Ala Gln Pro Ala Thr Ala Asp Tyr Tyr Ile Val Thr Cys Cys His Thr
        210                 215                 220

Cys Asn Thr Thr Val Arg Leu Cys Val Asn Ser Thr Ala Ser Asp Leu
225                 230                 235                 240

Arg Thr Ile Gln Gln Leu Leu Met Gly Thr Val Asn Ile Val Cys Pro
                245                 250                 255

Thr Cys Ala Gln Leu
            260
```

<210> SEQ ID NO 7
<211> LENGTH: 835
<212> TYPE: DNA
<213> ORGANISM: Artificial Sequence
<220> FEATURE:
<223> OTHER INFORMATION: HPV58 E6E7 DNA sequence

<400> SEQUENCE: 7

```
ggtaccgttt aaacggatcc gccaccatgg actggacctg gattctgttc ctggtggccg      60
ctgctacccg ggtgcacagc ttccaggatg ccgaggaaag cggccggacc ctgcacgatc     120
tgtgccaggc cctggaaacc agcgtgcacg agatcgagct gaagtgcgtg aatgcaagaa     180
aaaccctgca gcggagcgag gtgtacgacg ccgacctgcg gatcgtgtac gggacggcaa     240
ccccttcgc cgtgtgcaaa gtgtgcctgc ggctgctgag caagatcagc gagtaccggc     300
actacaacta cagcctgtac ggcgacaccc tggaacagac cctgaagaag tgcctgaacg     360
agatcctgat ccggtgcatc atctgccagc ggcccctgaa gcggcacgtg gacctgaaca     420
agcggttcca caacatcagc ggccggtgga ccggcagatg cgccgtgtgt ggaggcccag     480
gcggagacac gacccaggtg cgcggcagaa agcggcggag cagaggcaac aaccccaccc     540
tgagagagta catcctggac ctgcaccccg agcccaccga cctgtttggc tacggccagc     600
```

```
tgtgcgacag cagcgacgag gacgagatcg gcctggacgg ccctgatgga caggcccagc    660
ccgccaccgc caactactac atcgtgacct gctgctacac ctgtggcacc accgtgcggc    720
tgtgcatcaa cagcaccacc accgacgtgc gcaccctgca gcagctcctg atgggcacct    780
gtaccatcgt gtgccccagc tgcgcccagc agtgactcga ggcggccgcg agctc         835
```

```
<210> SEQ ID NO 8
<211> LENGTH: 262
<212> TYPE: PRT
<213> ORGANISM: Artificial Sequence
<220> FEATURE:
<223> OTHER INFORMATION: HPV58 E6E7 protein sequence

<400> SEQUENCE: 8
```

Met Asp Trp Thr Trp Ile Leu Phe Leu Val Ala Ala Thr Arg Val
1               5                   10                  15

His Ser Phe Gln Asp Ala Glu Glu Ser Gly Arg Thr Leu His Asp Leu
            20                  25                  30

Cys Gln Ala Leu Glu Thr Ser Val His Glu Ile Glu Leu Lys Cys Val
        35                  40                  45

Glu Cys Lys Lys Thr Leu Gln Arg Ser Glu Val Tyr Asp Ala Asp Leu
    50                  55                  60

Arg Ile Val Tyr Arg Asp Gly Asn Pro Phe Ala Val Cys Lys Val Cys
65                  70                  75                  80

Leu Arg Leu Leu Ser Lys Ile Ser Glu Tyr Arg His Tyr Asn Tyr Ser
                85                  90                  95

Leu Tyr Gly Asp Thr Leu Glu Gln Thr Leu Lys Lys Cys Leu Asn Glu
            100                 105                 110

Ile Leu Ile Arg Cys Ile Ile Cys Gln Arg Pro Leu Lys Arg His Val
        115                 120                 125

Asp Leu Asn Lys Arg Phe His Asn Ile Ser Gly Arg Trp Thr Gly Arg
    130                 135                 140

Cys Ala Val Cys Trp Arg Pro Arg Arg Gln Thr Gln Val Arg Gly
145                 150                 155                 160

Arg Lys Arg Arg Ser Arg Gly Asn Asn Pro Thr Leu Arg Glu Tyr Ile
                165                 170                 175

Leu Asp Leu His Pro Glu Pro Thr Asp Leu Phe Gly Tyr Gly Gln Leu
            180                 185                 190

Cys Asp Ser Ser Asp Glu Asp Glu Ile Gly Leu Asp Gly Pro Asp Gly
        195                 200                 205

Gln Ala Gln Pro Ala Thr Ala Asn Tyr Tyr Ile Val Thr Cys Cys Tyr
    210                 215                 220

Thr Cys Gly Thr Thr Val Arg Leu Cys Ile Asn Ser Thr Thr Thr Asp
225                 230                 235                 240

Val Arg Thr Leu Gln Gln Leu Leu Met Gly Thr Cys Thr Ile Val Cys
                245                 250                 255

Pro Ser Cys Ala Gln Gln
            260

```
<210> SEQ ID NO 9
<211> LENGTH: 54
<212> TYPE: DNA
<213> ORGANISM: Artificial Sequence
<220> FEATURE:
<223> OTHER INFORMATION: IgE Leader DNA sequence

<400> SEQUENCE: 9
```
atggactgga cctggatcct gttcctggtg gccgctgcca cacgggtgca cagc    54

<210> SEQ ID NO 10
<211> LENGTH: 18
<212> TYPE: PRT
<213> ORGANISM: Artificial Sequence
<220> FEATURE:
<223> OTHER INFORMATION: IgE leader protein

<400> SEQUENCE: 10

Met Asp Trp Thr Trp Ile Leu Phe Leu Val Ala Ala Thr Arg Val
1               5                   10                  15

His Ser

<210> SEQ ID NO 11
<211> LENGTH: 15
<212> TYPE: PRT
<213> ORGANISM: Artificial Sequence
<220> FEATURE:
<223> OTHER INFORMATION: HPV6 peptide 7

<400> SEQUENCE: 11

Thr Ala Glu Ile Tyr Ser Tyr Ala Tyr Lys Gln Leu Lys Val Leu
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: HPV11 peptide 7

<400> SEQUENCE: 12

Thr Ala Glu Ile Tyr Ala Tyr Ala Tyr Lys Asn Leu Lys Val Val
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: HPV11 peptide 27

<400> SEQUENCE: 13

His Cys Tyr Glu Gln Leu Glu Asp Ser Ser Glu Asp Glu Val Asp
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: HPV subdominant peptide 6

<400> SEQUENCE: 14

Phe Cys Lys Asn Ala Leu Thr Thr Ala Glu Ile Tyr Ser Tyr Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: HPV subdominant peptide 9

<400> SEQUENCE: 15

-continued

```
Leu Phe Arg Gly Gly Tyr Pro Tyr Ala Ala Cys Ala Cys Cys Leu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: HPV subdominant peptide 13

<400> SEQUENCE: 16

Tyr Ala Gly Tyr Ala Thr Thr Val Glu Glu Glu Thr Lys Gln Asp
1               5                   10                  15
```